US008211712B2

(12) United States Patent
Cho et al.

(10) Patent No.: US 8,211,712 B2
(45) Date of Patent: Jul. 3, 2012

(54) METHOD OF FABRICATING LIPID BILAYER MEMBRANES ON SOLID SUPPORTS

(75) Inventors: Nam-Joon Cho, Stanford, CA (US);
Curtis W. Frank, Cupertino, CA (US);
Jeffrey S. Glenn, Palo Alto, CA (US);
Kwang Ho Cheong, Giheung-Gu (KR)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 711 days.

(21) Appl. No.: 11/887,669

(22) PCT Filed: Mar. 29, 2006

(86) PCT No.: PCT/US2006/012085
§ 371 (c)(1),
(2), (4) Date: Apr. 23, 2009

(87) PCT Pub. No.: WO2006/110350
PCT Pub. Date: Oct. 19, 2006

(65) Prior Publication Data
US 2009/0263670 A1  Oct. 22, 2009

Related U.S. Application Data

(60) Provisional application No. 60/666,647, filed on Mar. 29, 2005.

(51) Int. Cl.
*G01N 33/543* (2006.01)
(52) U.S. Cl. ..................................................... 436/518
(58) Field of Classification Search .................. None
See application file for complete search history.

(56) References Cited

U.S. PATENT DOCUMENTS

| | | | |
|---|---|---|---|
| 5,364,851 A | 11/1994 | Joran | |
| 5,502,022 A | 3/1996 | Schwarz et al. | |
| 5,521,702 A * | 5/1996 | Salamon et al. | 356/244 |
| 5,846,814 A * | 12/1998 | Galla et al. | 435/287.2 |
| 6,306,598 B1 | 10/2001 | Charych et al. | |
| 6,306,958 B1 | 10/2001 | Dirschl et al. | |
| 6,344,436 B1 * | 2/2002 | Smith et al. | 514/7.4 |
| 6,756,078 B2 * | 6/2004 | Bookbinder et al. | 427/407.2 |
| 2005/0201973 A1 * | 9/2005 | Virtanen et al. | 424/78.27 |
| 2005/0250158 A1 * | 11/2005 | Parikh et al. | 435/7.1 |
| 2006/0068503 A1 * | 3/2006 | Cuppoletti | 436/518 |
| 2006/0068504 A1 * | 3/2006 | Kogi | 436/518 |
| 2007/0224637 A1 * | 9/2007 | McAuliffe et al. | 435/7.1 |
| 2007/0224639 A1 * | 9/2007 | Matsushita et al. | 435/7.1 |
| 2008/0033190 A1 * | 2/2008 | Lee et al. | 554/124 |
| 2008/0125367 A1 | 5/2008 | Glenn et al. | |
| 2011/0091864 A1 * | 4/2011 | Karlsson et al. | 435/4 |

OTHER PUBLICATIONS

"Intact Vesicle Adsorption and Supported Biomembrane Formation from Vesicles in Solution: Influence of Surface Chemistry, Vesicle Size, Temperature, and Osmotic Pressure" Reimhult et al., Langmuir, 2003, 19 (5), pp. 1681-1691.*
Reimhult et al., "Intact Vesicle Adsorption and Supported Biomembrane Formulation from Vesicles in Solution: Influence of Surface Chemistry, Vesicle Size, Temperature, and Osmotic Pressure", *Langmuir*, 2003, vol. 19, No. 5: 1681-1691.
Manoil et al., "Membrane Protein Assembly: Genetic, Evolutionary and Medical Perspectives", *Annual Review of Genetics*, 1995, vol. 29:131-150.
Srinivas, et al., "Membrane Interactions of Synthetic Peptides Corresponding to Amphipathic Helical Segments of the Human Immunodeficiency Virus Type-1 Envelope Gycoprotein", *Journal of Biological Chemistry*, 1992, vol. 267:7121-7127.
Elazar et al., "Amphipathic Helix-Dependent Localization of NS5A Mediates Hepatitis C Virus RNA Replication", *Journal of Virology*, 2003, vol. 77:6055-6061.

* cited by examiner

*Primary Examiner* — Ann Lam
(74) *Attorney, Agent, or Firm* — Paula A. Borden; Bozicevic, Field & Francis LLP.

(57) ABSTRACT

The present invention provides a method of producing a planar lipid bilayer on a solid support. With this method, a solution of lipid vesicles is first deposited on the solid support. Next, the lipid vesicles are destabilized by adding an amphipathic peptide solution to the lipid vesicle solution. This destabilization leads to production of a planar lipid bilayer on the solid support. The present invention also provides a supported planar lipid bilayer, where the planar lipid bilayer is made of naturally occurring lipids and the solid support is made of unmodified gold or titanium oxide. Preferably, the supported planar lipid bilayer is continuous. The planar lipid bilayer may be made of any naturally occurring lipid or mixture of lipids, including, but not limited to phosphatidylcholine, phosphatidylethanolamine, phosphatidylserine, phosphatidylinsitol, cardiolipin, cholesterol, and sphingomyelin.

4 Claims, 4 Drawing Sheets

# METHOD OF FABRICATING LIPID BILAYER MEMBRANES ON SOLID SUPPORTS

CROSS REFERENCE TO RELATED APPLICATIONS

This application is a national stage filing under 35 U.S.C. §371 of International Patent Application Ser. No. PCT/US2006/012085, which was filed on Mar. 29, 2006 and which was published in English under PCT Article 21(2) as WO 2006/110350 on Oct. 19, 2006, which International Patent Application claims benefit of priority of U.S. Provisional Patent Application Ser. No. 60/666,647, filed Mar. 29, 2005, which applications are incorporated herein by reference in their entirety.

FEDERALLY-SPONSORED RESEARCH OR DEVELOPMENT

This invention was made with Government support under contracts NAG-8-1843 awarded by the NASA Marshall Space Flight Center and 0213618 awarded by the National Science Foundation. The Government has certain rights in this invention.

FIELD OF THE INVENTION

The present invention relates generally to lipid membranes. More particularly, the present invention relates to methods of fabricating lipid bilayer membranes on solid supports.

BACKGROUND

Supported lipid bilayers formed by the fusion of small unilamellar vesicles onto silicon oxide or organic film-modified surfaces enable the biofunctionalization of inorganic solids, such as semiconductors, gold-covered surfaces, and optoelectronic and lab-on-a-chip devices. They have proven valuable in the study of the characteristics and behavior of membrane-bound proteins, membrane-mediated cellular processes, protein-lipid interactions, and biological signal transduction. Because of the complexity of biomembranes, there is a clear need to develop model membrane systems, where one or a few membrane components can be isolated and studied. In addition, a wide range of available surface-sensitive techniques can be used to study natural biological systems effectively by supporting model membranes on a solid surface. Applications of supported membranes on solid surfaces potentially include biosensors, programmed drug delivery, the acceleration and improvement of medical implant acceptance, and the production of catalytic interfaces.

In order to mimic natural biological systems, researchers have employed vesicle fusion methods to form supported bilayers on substrates such as glass, mica, self-assembled monolayers, and quartz. However, it has proven problematic to create planar lipid bilayers on preferred solid substrates, such as gold and $TiO_2$. For example, scientists have attempted to modify gold surfaces using self-assembled monolayers (SAMs), which may require special synthesis, but the structure of the SAMs that are formed may not be well-defined. Accordingly, there is a need in the art to develop new methods of forming supported bilayers on preferred substrates.

SUMMARY OF THE INVENTION

The present invention provides a method of producing a planar lipid bilayer on a solid support. With this method, a solution of lipid vesicles is first deposited on the solid support. Next, the lipid vesicles are destabilized by adding an amphipathic peptide solution to the lipid vesicle solution. This destabilization leads to production of a planar lipid bilayer on the solid support. Preferably, the amphipathic peptide is an alpha-helical peptide. More preferably, the alpha-helical peptide is a polypeptide having the entirety or a portion of the sequence SEQ ID NO: 1.

The present invention also provides a supported planar lipid bilayer, where the planar lipid bilayer is made of naturally occurring lipids and the solid support is made of unmodified gold or titanium oxide. Preferably, the supported planar lipid bilayer is continuous. The planar lipid bilayer may be made of any naturally occurring lipid or mixture of lipids, including but not limited to phosphatidylcholine, phosphatidylethanolamine, phosphatidylserine, phosphatidylinositol, cardiolipin, cholesterol, and sphingomyelin.

BRIEF DESCRIPTION OF THE FIGURES

The present invention together with its objectives and advantages will be understood by reading the following description in conjunction with the drawings, in which.

DETAILED DESCRIPTION OF THE INVENTION

Figure 1:
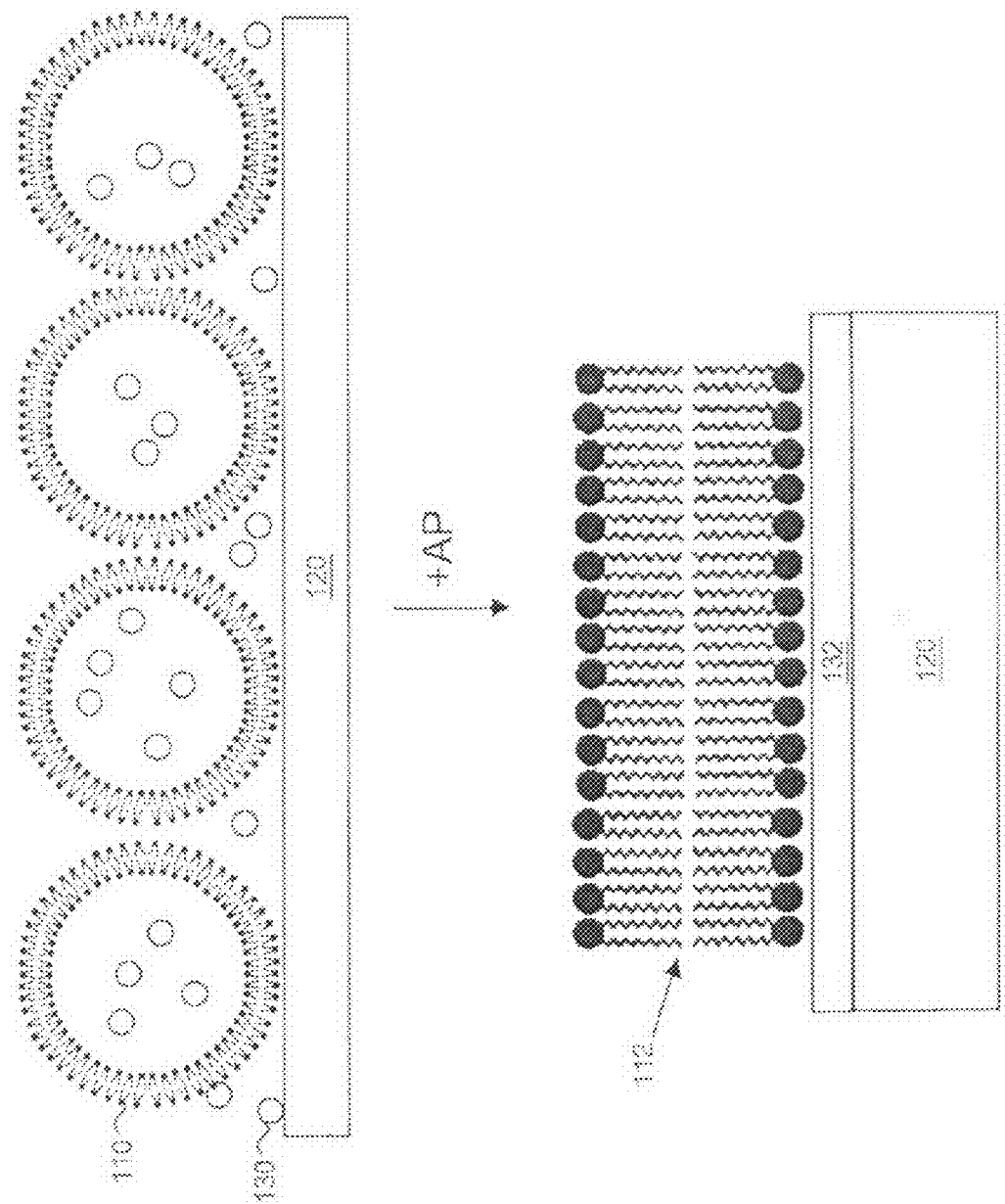
FIG. 1 shows a method of producing a planar lipid bilayer according to the present invention.

FIG. 1 illustrates a schematic of a method according to the present invention. FIG. 1A shows lipid vesicles 110 that have been deposited onto solid substrate 120. The vesicles have adsorbed to solid substrate 120. A large amount of water, indicated by circles 130, is trapped within the intact vesicles as well as between vesicles adsorbed on the surface of solid substrate 120. After addition of an amphipathic peptide (AP) solution (FIG. 1B), the vesicles are destabilized and ruptured, allowing the ruptured vesicles to fuse and form planar bilayer 112. When planar bilayer 112 forms, water 130 trapped within vesicles 112 is dispersed to form water layer 132.

The amphipathic peptide is preferably an alpha-helical peptide. More preferably, the amphipathic peptide is the AH peptide of the HCV nonstructural protein NS5A. This peptide is conserved across HCV isolates and has the sequence SEQ ID NO: 1. Either the entire peptide, amino acids 1-16 of the peptide (AH_S1), or amino acids 17-31 of the peptide (AH_S2) may be used to destabilize the lipid vesicles. Alternatively, the peptide may not have the exact sequence of SEQ ID NO: 1, as long as its amphipathic alpha-helical nature is preserved. For example, as shown by circular dichroism, the peptide may have a sequence that is at least about 80% identical to SEQ ID NO: 1, while still maintaining alpha-helicity. Preferably, the concentration of amphipathic peptide in the peptide solution is between about 0.05 µg/ml to 0.5 µg/ml. The amphipathic peptide may be contained in a variety of solvents, including biological buffers (such as Tris buffer, PBS buffer, and HEPES Buffer) and dimethylsulfoxide (DMSO).

Lipid vesicles suitable for the present invention are preferably between about 25 nm and about 80 nm in diameter. The vesicles may be prepared using any method known in the art, including but not limited to extrusion methods. The vesicles are preferably at a concentration of about 0.05 mg/ml to about 5 mg/ml in a biological buffer, such as Tris, PBS, and HEPES buffer, with NaCl concentration of about 100 mM to about 250 mM. Any lipid or mixture of lipids may be used to form the lipid vesicles, including but not limited to phospholipids. Preferred lipids are phosphatidylcholine, phosphatidylethanolamine, phosphatidylserine, phosphatidylinositol, cardiolipin, cholesterol, and sphingomyelin.

Any solid support may be used according to the present invention. Example materials include, but are not limited to silicon-containing materials, gold, platinum, and titanium oxide.

The present invention also provides supported planar lipid bilayers produced using the method of the present invention. Preferably, the lipid bilayer is composed of naturally occurring lipids and the solid support is made of unmodified gold or titanium oxide. Any naturally occurring lipid may be used for the bilayer, such as phospholipids. Preferred lipids are phosphatidylcholine, phosphatidylethanolamine, phosphatidylserine, phosphatidylinositol, cardiolipin, cholesterol, and sphingomyelin. Preferably, planar lipid bilayers according to the present invention are continuous, i.e. there are no gaps in the layer.

EXAMPLES

Formation of a Planar Lipid Bilayer on a Sold Substrate

Bilayer formation from intact vesicles was characterized using a quartz crystal microbalance-dissipation (QCM-D) instrument. To interpret the QCM-D results, a linear relationship between $\Delta f$ and adsorbed mass ($\Delta m$) derived from the classical Sauerbrey equation was employed:

$$\Delta m = -\frac{C}{n}\Delta f \qquad \text{Equation (1)}$$

where C is the mass-sensitivity constant with value 17.7 ngcm$^{-2}$Hz$^{-1}$ for the QCM-D crystal at 5 MHz, and n is the overtone number (n=1 for the fundamental and 3, 5, 7 for the overtones). The QCM-D has been used in numerous studies of the vesicle fusion process, where the dissipation is used to distinguish between rigid lipid bilayers and monolayers and soft deformable vesicles (see, e.g., Keller and Kasemo, "Surface specific kinetics of lipid vesicle adsorption measured with a quartz crystal microbalance", Biophys J. 1998 Sep; 75(3):1397-1402).

In order to investigate the ability of AH peptides to rupture vesicles, we tested unilamellar vesicles of 1-palmitoyl-2-oleoyl-sn-glycero-3-phosphocholine (POPC) extruded through 30 nm polycarbonate etch-tracked (PEC) membranes on a gold surface in the absence of the AH peptide, then applied the peptide to form a bilayer. When vesicles adsorb, a large amount of trapped water exists within the intact vesicles as well as between vesicles adsorbed on the surface. This trapped water is able to dissipate a large amount of energy, unlike the water that rests on top of a bilayer. This change in energy dissipation can in turn be used to track the transition between an intact vesicle and a bilayer.

Figure 2:
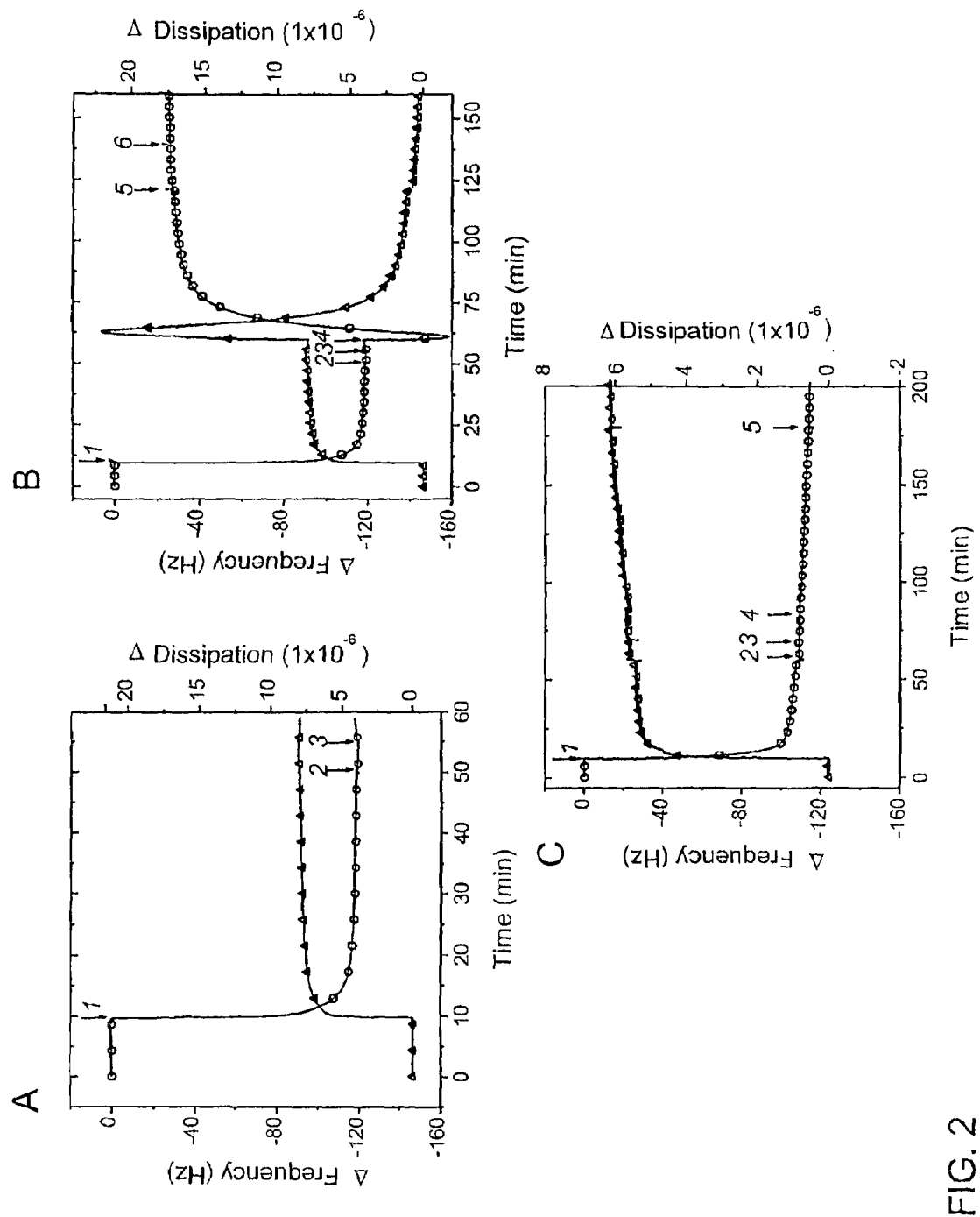
FIG. 2 shows quartz crystal microbalance-dissipation (QCM-D) analysis of planar lipid bilayer formation on a gold substrate according to the present invention.

In FIG. 2, $\Delta f(t)$ (triangles) and $\Delta D(t)$ (circles) show change in frequency and change in dissipation. FIG. 2A shows vesicle adsorption on an oxidized gold surface. After 10 min (arrow 1) of stabilizing the frequency signal, the POPC vesicle solution (0.1 mg/ml, $\varnothing_{30nm\ PEC}$=59 nm ±0.2 nm) was injected into a liquid cell. After 50 and 55 min (arrows 2 and 3), the same buffer that was used to dilute the vesicles (10 mM Tris (pH 7.5), 150 mM NaCl solution with 1 mM EDTA in 18.2 MΩ-cm MilliQ water (MilliPore, Oreg., USA) was used to wash the substrate twice and the stability of the intact vesicles on the gold surface was observed. As shown in FIG. 2B, at 60 min (arrow 4), an amphipathic_-helix peptide (AH peptide) solution was added (0.05 µg/ml) to the intact vesicles ($\varnothing_{30nm\ PEC}$=59 nm ±0.2 nm) on the gold surface. The peptide destabilized and ruptured the vesicles, making a complete bilayer. This is reflected in a decrease of frequency of 25.5 Hz ±0.5, with a maximum decrease of dissipation of as much as 0.08×10$^{-6}$ observed. After 120 and 140 min (arrows 5 and 6), the vesicle buffer was used to wash the substrate twice and the stability of the bilayers on the gold surface was observed. According to the Sauerbrey equation, from which the bilayer thickness can be calculated, these QCM-D parameters indicate the transition of the vesicles to a thin and rigid bilayer film.

In FIG. 2C, the effect of a non-amphipathic non-helical peptide (NH peptide) was examined. Unlike the AH peptide, the NH peptide has three charged amino acids spaced at intervals along the predicted N-terminal helix such that no sustained hydrophobic patch remains. The NH peptide has an Asp rather than a Val at residue 8, a Glu instead of an Ile at residue 12, and an Asp instead of a Phe at residue 19 of SEQ ID NO:1. In FIG. 2C, after 10 nm (arrow 1) of stabilizing the frequency signal, the POPC vesicle solution (0.1 mg/ml, $\varnothing_{30nm\ PEC}$=59 nm ±0.2 nm) was applied to the liquid cell. After 60 and 70 min (arrows 2 and 3), the vesicle buffer was used to wash the substrate twice and the stability of the intact vesicles on the gold surface was observed. At 85 min (arrow 4), the NH peptide solution was added (0.05 µg/ml) to the intact vesicles on the gold surface. The NH peptide does not show any evidence of having destabilized and ruptured the vesicles. After 160 min (arrow 5), the vesicle buffer was used to wash the substrate twice and the stability of the intact vesicles on the gold surface was observed.

Formation of a Planar Lipid Bilayer on a TiO$_2$ Substrate

Figure 3:
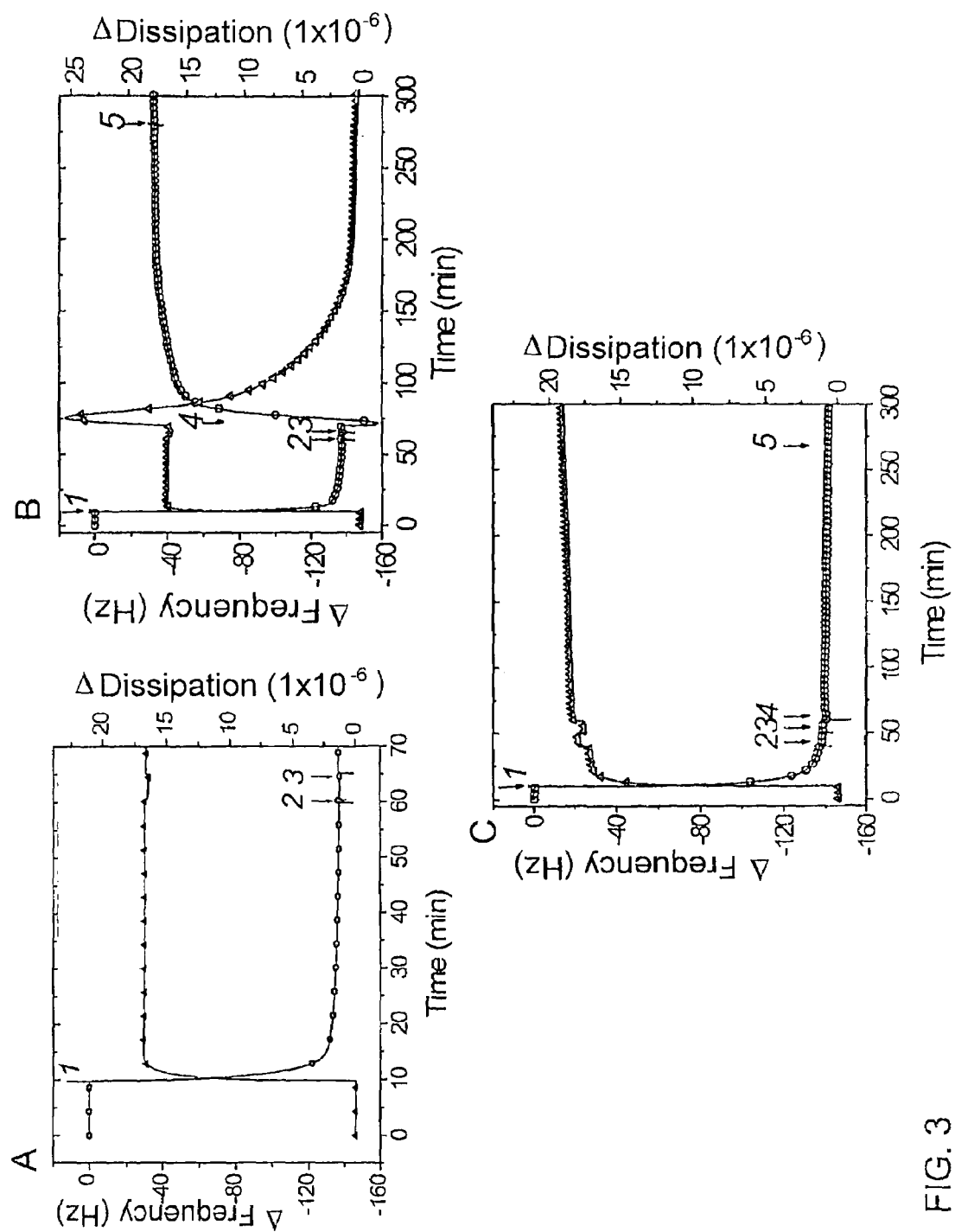
FIG. 3 shows QCM-D analysis of planar lipid bilayer formation on a $TiO_2$ substrate according to the present invention.

In order to investigate the ability of AH peptides to rupture vesicles on a TiO$_2$ surface, we tested unilamellar vesicles of POPC extruded through 30 nm PEC membranes on a TiO$_2$ surface in the absence of the AH peptide, then applied the peptide to form a bilayer (FIG. 3). In FIG. 3, $\Delta f(t)$ (triangles) and $\Delta D(t)$ (circles) show change in frequency and change in dissipation. FIG. 3A shows vesicle adsorption on a TiO$_2$ surface. After 10 min (arrow 1) of stabilizing the frequency signal, the POPC vesicle solution (0.1 mg/ml, $\varnothing_{30min\ PEC}$=59 nm ±0.2 nm) was injected into the liquid cell. After 60 and 65 min (arrows 2 and 3), the same buffer that was used to dilute the vesicles (10 mM Tris (pH 7.5); 150 mM NaCl solution with 1 mM EDTA in 18.2 MΩ-cm MilliQ water (MilliPore, Oreg., USA) was used to wash the substrate twice and the stability of the intact vesicles on the TiO$_2$ surface was observed. As shown in FIG. 3B, at 70 min (arrow 4), the AH peptide solution was added (0.05 µg/ml) to the intact vesicles ($\varnothing_{30nm\ PEC}$=59 nm ±0.2 nm) on the TiO$_2$ surface (FIG. 2B). The peptide destabilized and ruptured the vesicles, making a complete bilayer. After 270 min (arrow 5), the vesicle buffer was used to wash the substrate twice and the stability of the bilayers on the TiO$_2$ surface was observed.

In FIG. 3C, the effect of the NH peptide was examined. In FIG. 3C, after 10 min (arrow 1) of stabilizing the frequency signal, the POPC vesicle solution (0.1 mg/ml, $\varnothing_{30nm\ PEC}$=59 nm ±0.2 nm) was applied to the liquid cell. After 40 and 50 min (arrows 2 and 3), the vesicle buffer was used to wash the substrate twice and the stability of the intact vesicles on the TiO$_2$ surface was observed. At 60 min (arrow 4), the NH peptide solution was added (0.05 μg/ml) to the intact vesicles on the TiO$_2$ surface. The NH peptide does not show any evidence of having destabilized and ruptured the vesicles. After 270 min (arrow 5), the vesicle buffer was used to wash the substrate twice and the stability of the intact vesicles on the TiO$_2$ surface was observed.

the AH peptides ruptured vesicles to form bilayers (P ≦0.001). These results correlate with QCM-D kinetic data.

As one of ordinary skill in the art will appreciate, various changes, substitutions, and alterations could be made or otherwise implemented without departing from the principles of the present invention. Accordingly, the scope of the invention should be determined by the following claims and their legal equivalents.

---

SEQUENCE LISTING

```
<160> NUMBER OF SEQ ID NOS: 1

<210> SEQ ID NO 1
<211> LENGTH: 31
<212> TYPE: PRT
<213> ORGANISM: Hepatitis C virus

<400> SEQUENCE: 1

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Asp Tyr Lys Asp
            20                  25                  30
```

---

AFM Analysis of Lipid Bilayer Formation According to the Present Invention

Figure 4:
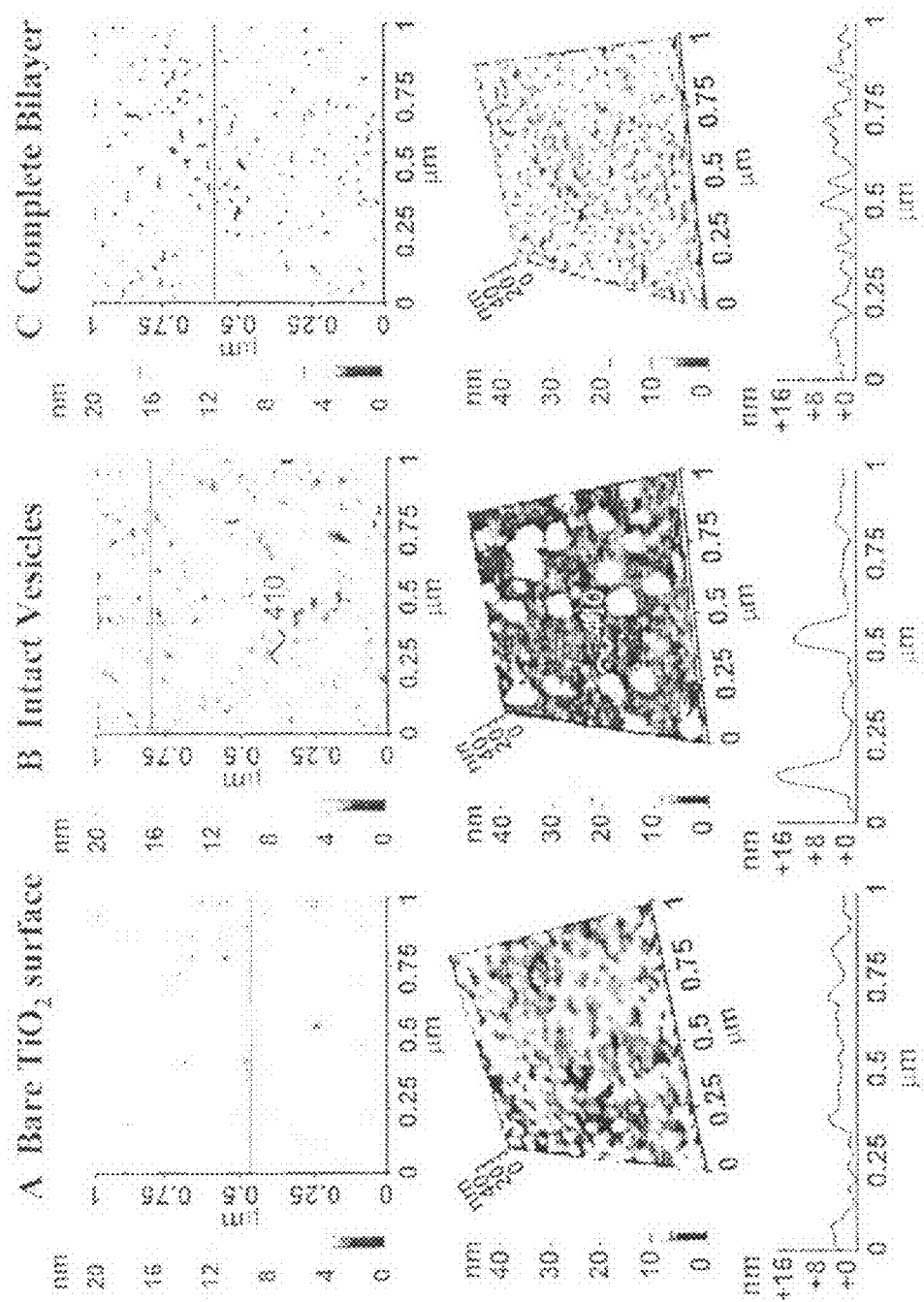
FIG. 4 shows atomic force microscopy (AFM) analysis of planar lipid bilayer formation on a $TiO_2$ substrate according to the present invention.

AFM was utilized in order to confirm and directly display rupture of vesicles and bilayer formation by the destabilizing agent the AH peptide. FIG. 4 shows the results of this analysis. For each column, the top image shows a top view in 2-D, the middle image shows a top view in 3-D, and the graph shows measurements taken along the black line shown in the top image. The images are presented in Height mode. Scans were taken in the direction indicated by the white arrow on FIG. 4A, top image.

In FIG. 4A, AFM was conducted on a bare TiO$_2$ surface in Tris buffer (150 mM NaCl, 10 mM Tris [pH 7.5], 1 mM EDTA) as a control. The bare TiO$_2$ surface showed an average root mean square roughness (Rq) of 1.63 ±0.12 nm (±S.E. n=15). 59 nm ±0.2 nm diameter POPC vesicles (0.1 mg/ml) were carefully added through the injection system, incubated for 30 minutes, and thoroughly rinsed three times with Tris buffer. Intact vesicles. such as vesicle 410, were clearly identified by AFM and the average Rq increased to 2.70 ±0.15 nm (±S.E. n=15), as shown in FIG. 4B. A grain analysis was applied in order to identify and count the vesicles. In order to minimize the effects of particles other than vesicles, only diameters between 50 to 100 nm hyperbolar-shaped objects were counted. The AFM images, as shown in FIG. 4B, and grain analysis were used to identify the sizes of thirteen vesicles. The vesicles had an average diameter of 74.57 ±4.07 nm (±S.E. n=13) and average volume of 3.32×10−5 μm$^3$ ±6.16×10−6 μm$^3$ (±S.E. n=13). Cross-sectional analysis displays the height of the vesicles to be approximately 15 nm.

The AFM images in FIG. 4C show the effect of the AH peptide on the vesicles as a destabilizing agent, which was examined by injecting the peptide (0.05 μg/ml) and incubating the solution for 2 hours prior to scanning the images. These images clearly confirm the QCM-D data, indicating that vesicles were ruptured as a result of the treatment by AH peptide at 0.05 μg/ml concentration after 120 minutes. The average Rq of 1.67 ±0.12 nm (±S.E. n=15) indicated the roughness became similar to the bare TiO$_2$ surface. Grain analysis identified no vesicle-like structures, indicating that

What is claimed is:

1. A supported planar lipid bilayer comprising:
   a) a planar lipid bilayer comprising naturally occurring lipids; and
   b) a solid support comprising unmodified gold or titanium oxide;
   wherein said lipid bilayer is supported by said solid support.

2. The supported planar lipid bilayer as set forth in claim 1, wherein said lipids are phospholipids.

3. The supported planar lipid bilayer as set forth in claim 1, wherein said lipids are selected from the group consisting of phosphatidylcholine, phosphatidylethanolamine, phosphatidylserine, phosphatidylinositol, cardiolipin, cholesterol, and sphingomyelin.

4. The supported planar lipid bilayer as set forth in claim 1, wherein said planar lipid bilayer is continuous.

* * * * *